United States Patent [19]

Srivatsa

[11] Patent Number: 5,338,306
[45] Date of Patent: Aug. 16, 1994

[54] CATHETER INTRODUCING DEVICE

[76] Inventor: Kadiyali M. Srivatsa, 125 Russell Court, Russell Square, London, WC1, England

[21] Appl. No.: 949,515

[22] PCT Filed: May 16, 1991

[86] PCT No.: PCT/GB91/00777
§ 371 Date: Nov. 16, 1992
§ 102(e) Date: Nov. 16, 1992

[87] PCT Pub. No.: WO91/17786
PCT Pub. Date: Nov. 28, 1991

[30] Foreign Application Priority Data

May 16, 1990 [GB] United Kingdom ............... 9010985

[51] Int. Cl.$^5$ ............................................. A61M 25/01
[52] U.S. Cl. ...................................... 604/165; 604/274
[58] Field of Search ............... 604/157, 158, 164, 143, 604/274, 165

[56] References Cited

U.S. PATENT DOCUMENTS

| Re. 25,279 | 10/1962 | Crockford et al. | 604/143 |
|---|---|---|---|
| 4,292,970 | 10/1981 | Hession, Jr. | |
| 4,311,137 | 1/1982 | Gerard | |
| 4,601,710 | 7/1986 | Moll | 604/274 |
| 4,744,786 | 5/1988 | Hooven | 604/143 |
| 5,186,712 | 2/1993 | Kelso et al. | 604/157 |
| 5,205,828 | 4/1993 | Kedem | 604/158 |
| 5,226,426 | 7/1993 | Yoon | 604/165 |

FOREIGN PATENT DOCUMENTS 2063679 6/1981 United Kingdom .

Primary Examiner—Paul J. Hirsch
Attorney, Agent, or Firm—Edwin D. Schindler

[57] ABSTRACT

A catheter introducing device comprises means (10) for holding a cannula (30) with a needle (20) inserted through it and with a tip (22) of the needle projecting from the cannula, and a biassing arrangement which is normally locked but when released urges the cannula forwardly and over the tip of the needle.

11 Claims, 4 Drawing Sheets

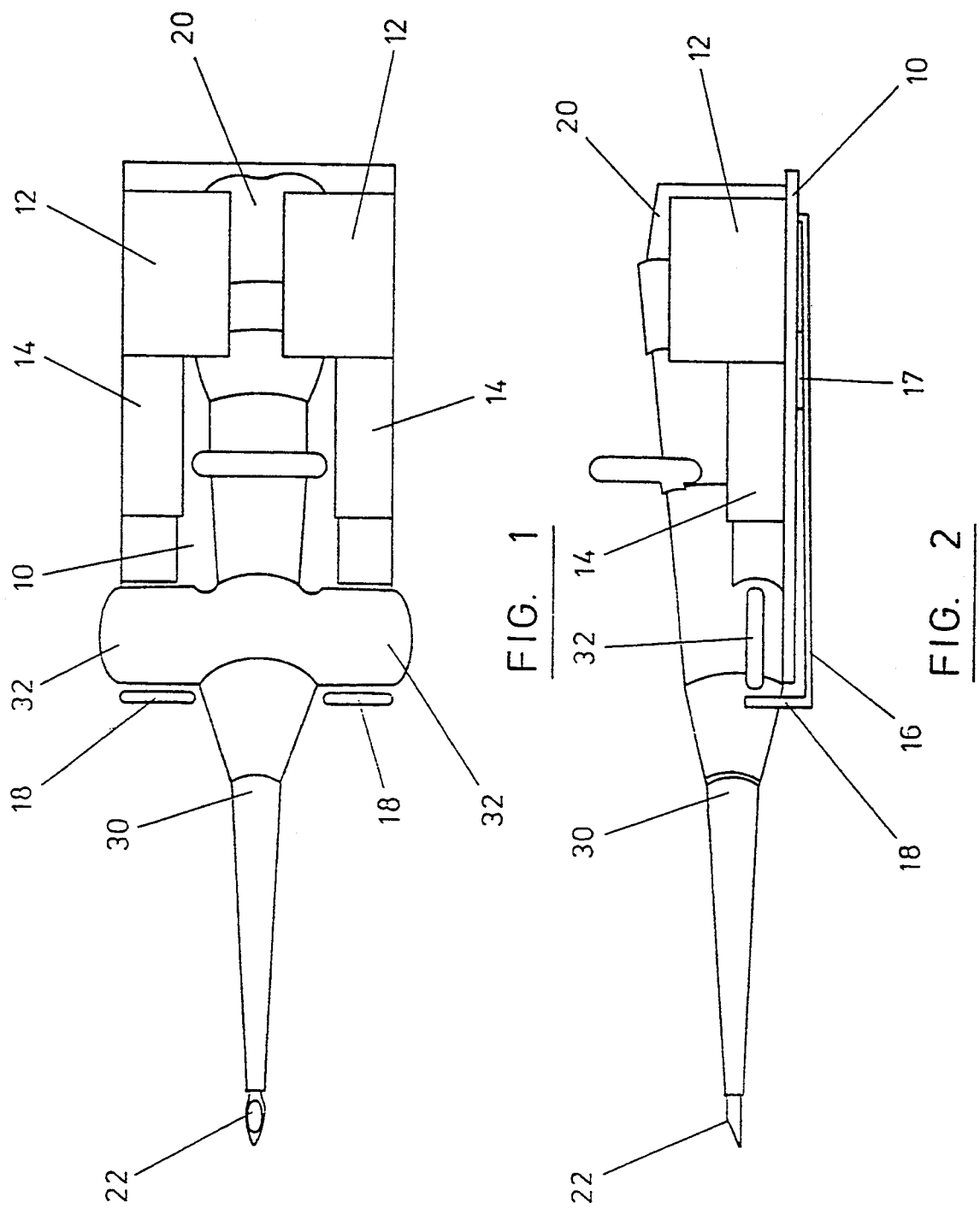

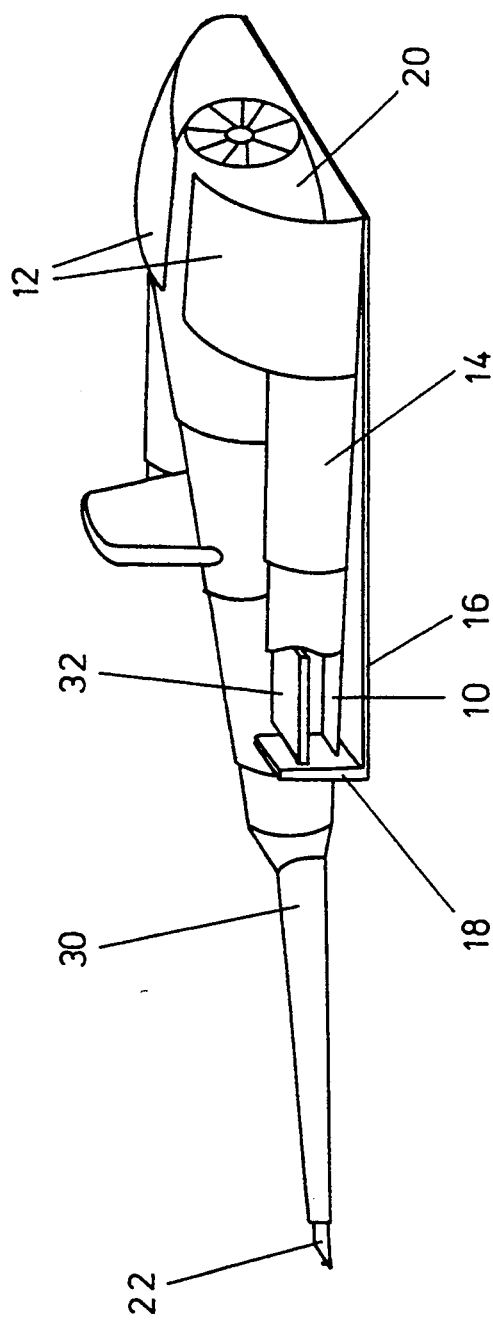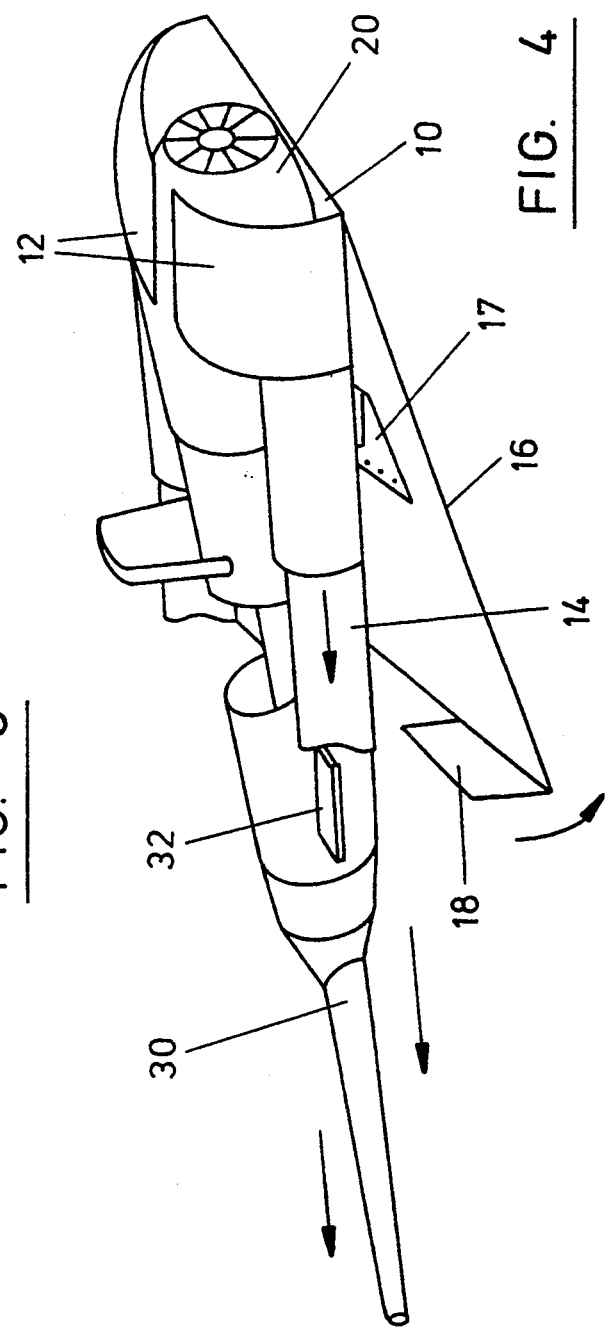

CATHETER INTRODUCING DEVICE

This invention relates to a device for introducing a catheter into a blood vessel of a patient.

Intravenous cannulisation is an important procedure particularly in managing acutely ill patients. The procedure is carried out using a needle inserted through the cannula so that its tip projects from the cannula, inserting the needle into an artery or vein, then advancing the cannula over the tip of the needle and into the artery or vein, and then withdrawing the needle. This procedure requires very fine hand control and considerable practice on the part of the doctor carrying it out. Cannulisation is occasionally complicated and takes time and places the patient under considerable stress.

I have now devised a catheter introducing device which overcomes these problems and enables a cannula to be introduced in a quick, easy and reliable manner.

In accordance with this invention, there is provided a catheter introducing device which comprises means for holding a cannula with a needle inserted through it and with a tip of the needle projecting from the cannula, and a biassing arrangement which is normally locked but when released urges the cannula forwardly and over the tip of the needle.

In using this device, the needle tip, projecting from the cannula, is inserted into the artery or vein. Then by releasing the biassing arrangement, the cannula 13 automatically displaced forwardly over the tip of the needle and into the artery or vein. The needle and the introducing device can now be withdrawn, leaving the cannula inserted into the blood vessel.

In one embodiment the biassing arrangement comprises two elements for pushing against two wings projecting from opposite sides of the cannula. Preferably the arrangement includes a locking element which normally engages these wings to prevent the cannula advancing over the needle. Preferably the locking element is spring-biassed to a release position and is held in its locking position by the user, then released when the needle tip has been inserted into the artery or vein.

The biassing arrangement may comprise a gas spring, including a plunger which when released forces the cannula forwardly under the pressure of compressed gas. The gas e.g. air may be compressed by the plunger being pushed into a sealed cylinder such that the gas inside the cylinder is compressed. The cannula itself may form the plunger. The catheter introducing device may be supplied with the cannula already loaded onto the needle in its biassed position. After the biassing arrangement has been released, the introducing device can be discarded.

In an alternative embodiment the locking element may engage the body of the cannula, thus the cannula with or without projecting wings can be inserted into the blood vessels.

Embodiments of this invention will now be described by way of examples only and with reference to the accompanying drawings, in which:

FIG. 1 is a plan view of an embodiment of catheter introducing device in accordance with this invention, shown with a cannula and its needle held in position;

FIG. 2 is a side view of the device;

FIG. 3 is a perspective view of the device in its locked condition;

FIG. 4 is a similar view of the device when the lock is released;

FIG. 6 in a sectional view of the device of FIG. 7, shown with the cannula partially removed from the device.

Figure 5:
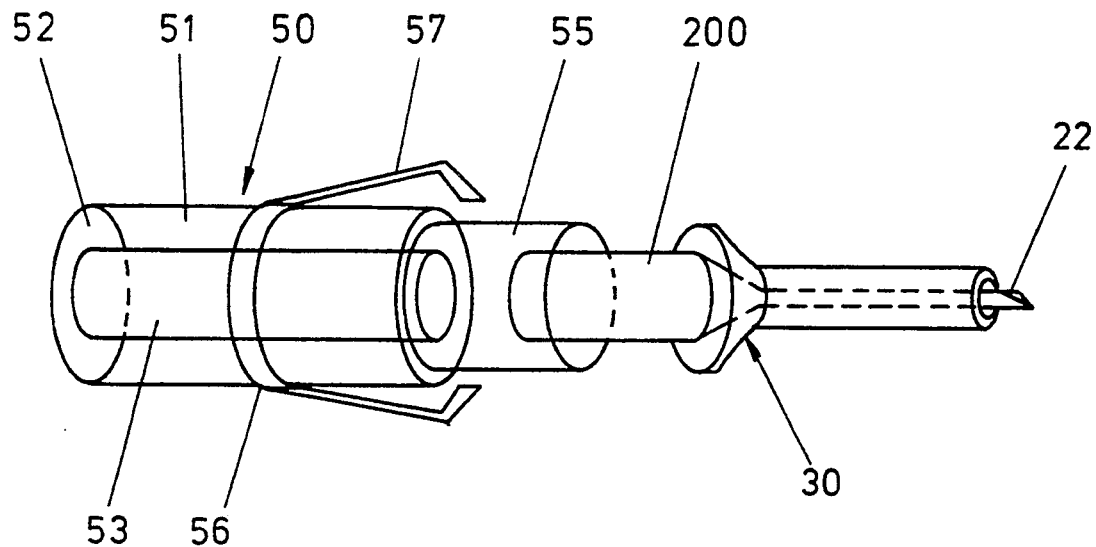
FIG. 5 is a perspective view of a further embodiment of catheter introducing device in accordance with this invention, shown with a cannula and its needle removed from the device.

Referring to the drawings, there is shown a catheter introducing device which has a flat rectangular base 10 having at one end (its rear end) a pair of projecting leaves 12 for holding an enlarged end 20 of the needle. Two spring-loaded telescopic pushing elements 14 extend along opposite edges of the base 10. A locking arrangement is mounted to the opposite side of the base 10 and comprises a flat plate 16 having one end pivoted to the base 10 adjacent its rear end, urged away by a spring 17 and having two upstanding flanges 18 at its opposite end.

The cannula 30 is of tapering, tubular form, and has two flat wings 32 projecting from opposite sides. The cannula 30, with the needle inserted through it and the tip 22 of the needle projecting from the narrower end of the cannula, is laid on the base 10 with the enlarged end 20 of the needle held by the leaves 12. The cannula has been slid rearwardly for its wings 32 to engage and depress the spring-loaded telescopic elements 14 and the locking plate 16 is held flat against the underside of the base 10 so that its flanges 18 engage the forward edges of the wings 32.

The user advances the assembly, in the condition shown in FIG. 3, to insert the tip of the needle into the artery or vein of the patient. Then he simply relaxes his grip on the locking plate 16 so that this pivots away from the base 1, the flanges 18 disengaging from the wings 32 of the cannula. The spring-loaded telescopic elements 14 immediately push the cannula forwardly over the tip of the needle and into the blood vessel, as indicated by the arrows in FIG. 4. The introducing device and needle are then withdrawn.

Figure 6:
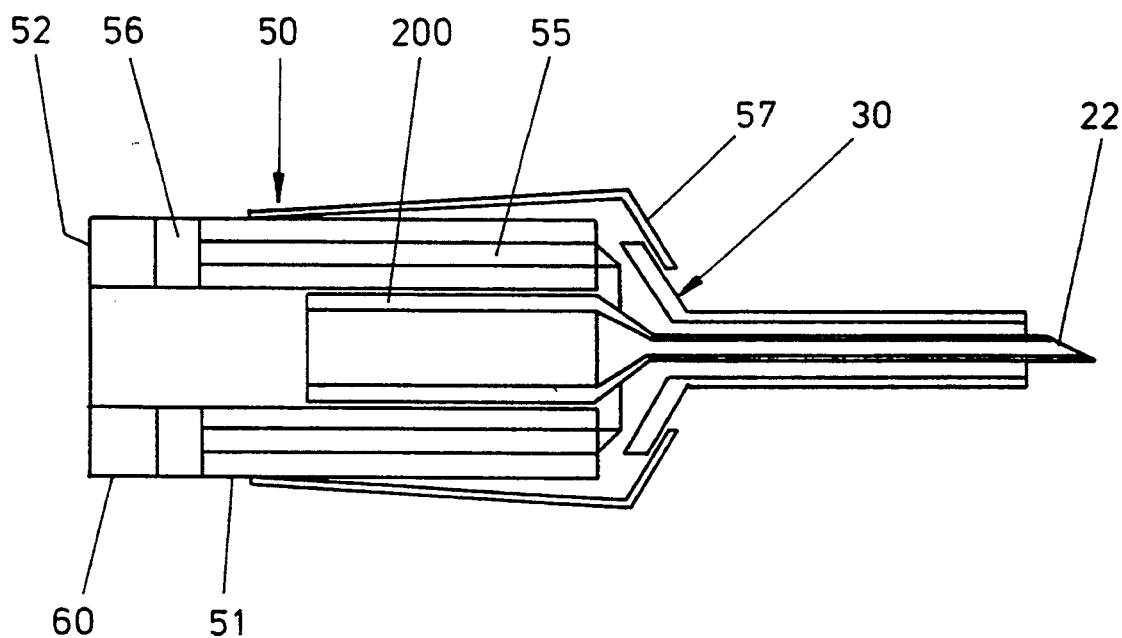
FIG. 6 is a sectional view of the device of FIG. 5 shown with the cannula and its needle held in position.

FIGS. 5 and 6 of the drawing show a second embodiment of catheter introducing device, and like parts are given like reference numerals. The device 50 comprises a transparent plastics material tube 51 having a sealed end 52, and an inner tube 53 formed co-axially within the tube 51. A tubular plunger 55 is formed with a rubber "O" ring 56 at one end, to slide into the space between the tubes 51 and 53. Spring-loaded locking elements 57 are attached to the outer wall of the tube 51.

In use, the plunger 55 is inserted into the tube 51 and the rubber "O" ring 56 fits tightly between the two co-axial tubes 51, 53. As the plunger 55 is pushed further along the tubes 51, 53 it compresses the air trapped in the space 60 between the sealed end of the tube 52 and the "O" ring 56.

A cannula 30, which may be formed without the wings of the previous embodiment, is used to push the plunger 55 fully inside the device. A needle 22 extends through the cannula and is formed at one end with a transparent collecting chamber 200 which is a push-fit within the inner tube 51. The wider end of the cannula 30 abuts the end of the plunger 55 and is engaged by two locking elements 57 to prevent the cannula 30 advancing over the needle.

The cannula 30 and needle are inserted into the artery or vein of the patient, as for the embodiment described above. The user may then relax his grip on the spring-loaded elements 57 so that the cannula 30 is pushed over the needle and further into the blood vessel by the plunger 55: the plunger 55 is pushed outwardly from the tubes 51, 53 owing to the compressed air contained in the space 60.

Figure 7:
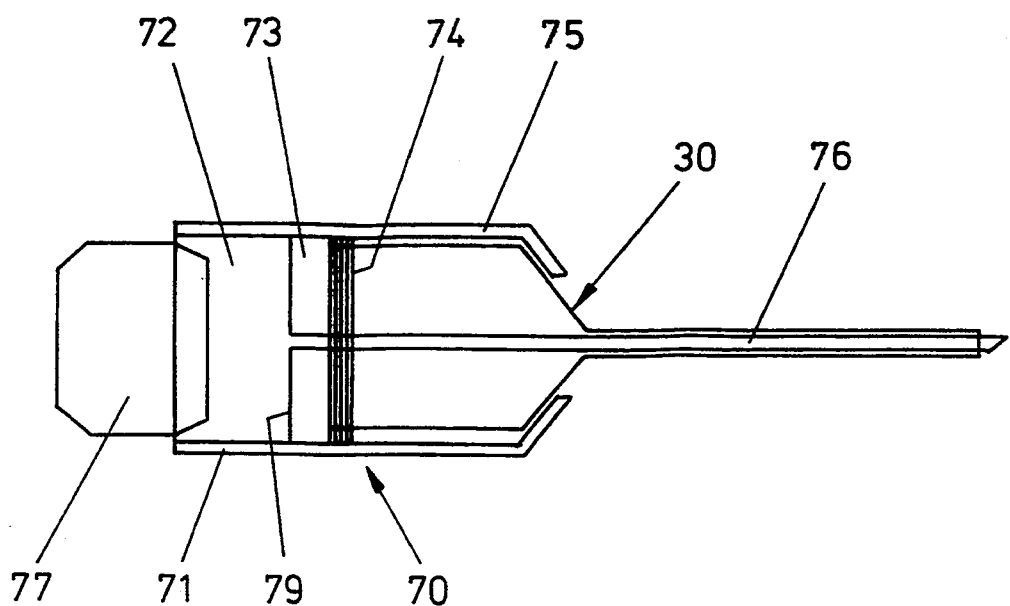
FIG. 7 is a sectional view of a further embodiment of catheter introducing device in accordance with the invention, shown with a cannula held in position.
Figure 8:
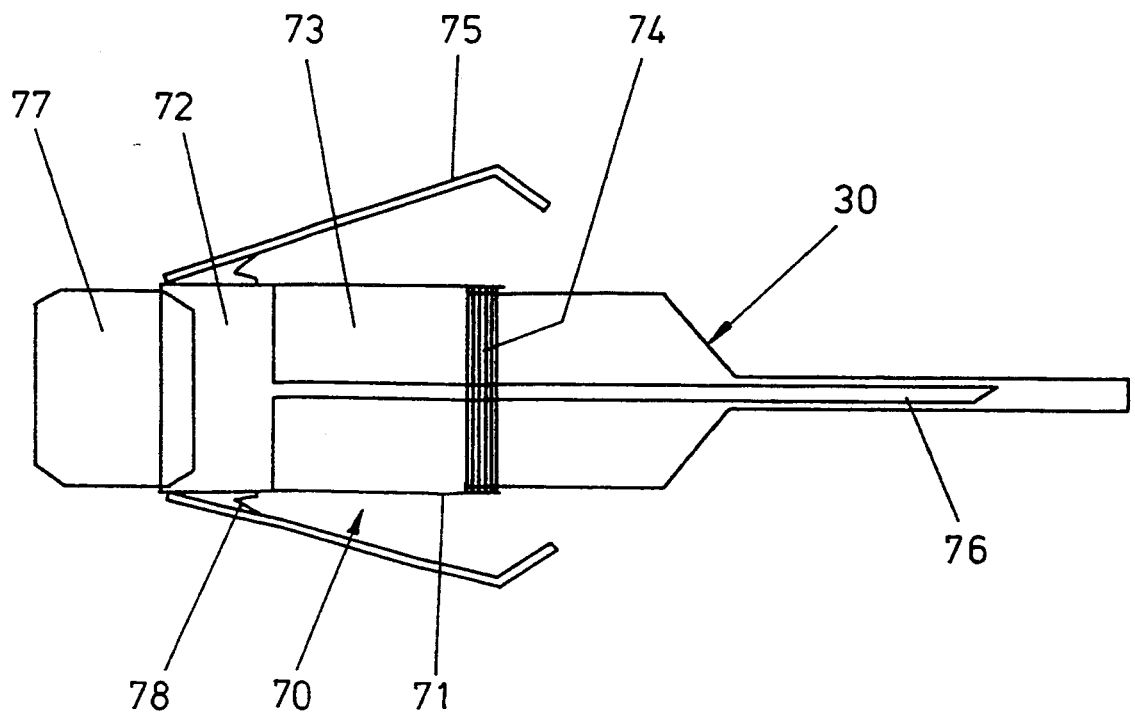

FIGS. 7 and 8 show an embodiment of catheter introducing device, which can be discarded after use.

The device 70 comprises a tube 71 having an end closed by a closure member 77. A wall 79 defines a chamber 72 at the end of the device. A needle 76 which opens into the chamber 72, projects outwardly from the wall 79 along the axis of the tube 71. Spring-loaded locking elements 75 are attached to the outer wall of the tube 71. During manufacture of the device a cannula 30, having a rubber cap 74 formed on its wider end, is push-fitted into the tube 71 such that the needle 76 sealingly pierces its rubber cap 74. As the cannula 30 is pushed into the tube 71, air is compressed in the space 73 between the rubber cap 74 and the chamber wall 79.

To hold the cannula 30 inside the tube 71 and contain the compressed air 73, the two locking elements 75 are held against the tube 71 so that they engage the cannula 30. A tear-off strip or clip (not shown) may be provided to hold the locking elements 75 in this condition.

In use the strip or clip is removed, and the user holds the two locking elements 57 in place. Once the needle and cannula have been inserted into the patient's blood vessel, the user can release the locking elements 57. The force of the compressed air 73 forces the cannula 30 forwardly over the needle and further into the patient's blood vessel. It will be appreciated that the rubber cap 74 prevents blood from escaping from the cannula 30 until a tube or needle has been connected to it.

Advantageously the chamber 72 fills with blood once the needle has entered the blood vessel, thus the user can be sure that the device is correctly positioned before the cannula is released.

The devices which have been described enable cannula to be introduced into arteries or veins in a quick, easy and reliable manner.

I claim:

1. A catheter introducing device, comprising:
    holding means for holding a needle and a cannula with said needle being inserted through said cannula and having its tip projecting forwardly from said cannula;
    biassing means acting on said cannula for biassing said cannula forwardly relative to said holding means and said needle; and,
    locking means normally engaged with said cannula for restraining said cannula against the bias of said biassing means, said locking means being releasable for allowing said biassing means to move said cannula forwardly over the tip of said needle.

2. The catheter introducing device as claimed in claim 1, further comprising additional means for biassing said locking means to a release position, said locking means being arranged to be held in its locking position by a user.

3. The catheter introducing device as claimed in claim 1, wherein said cannula comprises two wings projecting laterally from opposite sides thereof and wherein said biassing means comprises two biassing elements mounted to said holding means and acting on respective said wings of said cannula.

4. The catheter introducing device as claimed in claim 1, wherein said biassing means comprises a cylinder, a plunger fitted into said cylinder and compressed gas within said cylinder, said locking means normally restraining said plunger against movement under the influence of said compressed gas.

5. The catheter introducing device as claimed in claim 4, wherein an end of said cannula is formed with an elastomeric seal and forms said plunger fitted within said cylinder.

6. The catheter introducing device as claimed in claim 1, further comprising a transparent chamber connected to said needle and arranged for receiving blood through said needle when said needle is inserted into a blood vessel.

7. A catheter introducing device, comprising:
    holding means for holding a needle and a cannula with said needle being inserted through said cannula and having its tip projecting forwardly from said cannula, said cannula having two wings projecting laterally from opposite sides thereof;
    biassing means comprising two biassing elements mounted to said holding means and acting on respective said wings of said cannula; and,
    locking means for normally locking said biassing means, but releasable for said biassing means for moving said cannula forwardly over the tip of said needle.

8. The catheter introducing device as claimed in claim 7, further comprising additional means for biassing said locking means to a release position, said locking means being arranged to be held in its locking position by a user.

9. The catheter introducing device as claimed in claim 7, wherein said biassing means comprises a cylinder, a plunger fitted into said cylinder and compressed gas within said cylinder, said locking means normally restraining said plunger against movement under the influence of said compressed gas.

10. The catheter introducing device as claimed in claim 9, wherein an end of said cannula is formed with an elastomeric seal and forms said plunger fitted within said cylinder.

11. The catheter introducing device as claimed in claim 7, further comprising a transparent chamber connected to said needle and arranged for receiving blood through said needle when said needle is inserted into a blood vessel.

* * * * *